United States Patent [19]

Franks et al.

[11] Patent Number: 5,098,893
[45] Date of Patent: Mar. 24, 1992

[54] STORAGE OF MATERIALS

[75] Inventors: Felix Franks, Cambridge; Ross H. M. Hatley, Hardwick, both of England

[73] Assignee: Pafra Limited, Basildon, England

[21] Appl. No.: 479,939

[22] Filed: Feb. 12, 1990

[30] Foreign Application Priority Data

Feb. 16, 1989 [GB] United Kingdom ............... 8903593

[51] Int. Cl.⁵ .................. A61K 9/26; C12N 11/00; C07K 17/00
[52] U.S. Cl. ......................................... 514/54
[58] Field of Search .............. 424/440, 459, 461, 462, 424/80, 94.1, 94.3; 514/54, 970, 971, 948

[56] References Cited

U.S. PATENT DOCUMENTS

| | | | |
|---|---|---|---|
| 125,714 | 4/1872 | Allen | 424/440 |
| 586,504 | 7/1897 | Marcsch | 424/440 |
| 2,648,609 | 8/1953 | Wurster | 424/440 |
| 3,300,474 | 1/1967 | Flodin et al. | 536/120 |
| 3,413,198 | 11/1968 | Deutsch | 195/103.5 |
| 3,456,050 | 7/1969 | Rieckmann et al. | 424/440 |
| 3,480,468 | 11/1969 | Carletti et al. | 424/440 |
| 3,554,767 | 1/1971 | Daum et al. | 424/440 |
| 4,157,386 | 6/1979 | La Rochelle | 424/49 |
| 4,372,942 | 2/1983 | Cimiluca | 424/440 |
| 4,423,086 | 12/1983 | Devos et al. | 424/440 |
| 4,551,329 | 11/1985 | Harris et al. | 424/440 |
| 4,587,267 | 5/1986 | Drake et al. | 514/769 |
| 4,741,872 | 5/1988 | De Luca et al. | 424/94.3 |
| 4,749,575 | 6/1988 | Rotman | 424/440 |
| 4,753,790 | 6/1988 | Silva et al. | 424/440 |
| 4,762,719 | 8/1988 | Forester | 424/440 |
| 4,847,090 | 7/1989 | Della Posta et al. | 424/440 |
| 4,849,225 | 7/1989 | Mitsuhashi et al. | 424/440 |
| 4,863,865 | 9/1989 | Franks | 435/240.2 |
| 4,873,085 | 10/1989 | Fuisz | 424/440 |
| 4,891,319 | 1/1990 | Roser | 435/188 |
| 4,898,781 | 2/1990 | Onouchi et al. | 424/94.3 |
| 4,910,135 | 3/1990 | Tischer et al. | 435/28 |
| 4,963,359 | 10/1990 | Haslwanter et al. | 424/440 |
| 4,985,252 | 1/1991 | Jung et al. | 424/440 |
| 4,997,654 | 3/1991 | Corsello et al. | 424/440 |

FOREIGN PATENT DOCUMENTS

| | | |
|---|---|---|
| 252750 | 1/1988 | European Pat. Off. |
| 223221 | 3/1989 | European Pat. Off. |
| 244771 | 3/1989 | European Pat. Off. |
| 159826 | 3/1972 | Fed. Rep. of Germany |
| 70-12153B | 1/1970 | Japan |
| 8600336 | 1/1986 | World Int. Prop. O. |
| 8700196 | 1/1987 | World Int. Prop. O. |

OTHER PUBLICATIONS

Hatley et al., Biotechnology & Applied Biochemistry, 11, 367–370 (1989).
Polinsky et al., Proc. Natl. Acad. Sci. USA, 72, No. 9, 3310–3314 (1975).
Slade et al., Pure and Applied Chem., 60, No. 12, 1841–1864 (1988).
Hatley et al., Process Biochemistry, 169–172 (Dec. 1987).
Pure and Applied Chemistry, vol. 60, 1841–1864, Slade and Levine, "Non-Equilibrium Behaviour of Small Carbohydrate Water Systems".

*Primary Examiner*—Ronald W. Griffin
*Attorney, Agent, or Firm*—Abelman, Frayne & Schwab

[57] ABSTRACT

A material or mixture of materials which is not itself storage stable is rendered storage stable by incorporation into a water-soluble or swellable glassy or rubbery composition which can then be stored at ambient temperature. Recovery is by adding aqueous solution to the composition.

16 Claims, No Drawings

STORAGE OF MATERIALS

This invention relates to the stabilisation and storage of materials. The principal envisaged field of application is materials employed in the biochemical field and some pharmaceuticals.

A few biologically active materials (e.g. some proteins) are sufficiently stable that they can be isolated, purified and then stored in solution at room temperature. For most materials however this is not possible and some more elaborate form of stabilisation/storage procedure must be used.

A "repertoire" of techniques is known. Not all of them are useful for all materials that give rise to a storage problem. Known storage/stabilisation techniques which are applied to materials after isolation into an aqueous suspension or solution are:

(i) Addition of high concentration of chemical "stabilizer" to the aqueous solution or suspension. Typically 3M ammonium sulphate is used. However, such additives can alter the measured activity of enzymes and can give ambiguous or misleading results if the enzyme is used in a test procedure. (R. H. M. Hatley and F. Franks. Variation in apparent enzyme activity in two-enzyme assay systems: Phosphoenolpyruvate carboxylase and malate dehydrogenase. Biotechnol. Appl. Biochem. 11 367-370 (1989)). In the manufacture of diagnostic kits based on multi-enzyme assays, such additives often need to be removed before the final formulation. Such removal, by dialysis, often reduces the activity of an enzyme.

(ii) Freeze/thaw methods in which the preparation, usually mixed with an additive (referred to as a cryoprotectant) is frozen and stored, usually below $-50°$ C., sometimes in liquid nitrogen. Not all proteins will survive a freeze/thaw cycle.

(iii) Cold storage, with a cryoprotectant additive present in sufficient concentration (e.g. glycerol) to depress the freezing point to below the storage temperature and so avoid freezing. For example in the case of restriction endonucleases, the enzymes need to be protected against freezing by the addition of high concentrations of glycerol and maintained at $-20°$ C. Use of an additive in high concentration may also reduce the specificity of restriction enzymes and give rise to so-called "star-activity". (B. Polisky et al. PNAS USA, 72, 3310 (1975)).

(iv) The commonest method for the stabilisation of isolated protein preparations is freeze-drying, but this process can only be applied to freeze-stable products. The aqueous isolate of the active material in a suitable pH buffer and in the presence of a cryoprotectant is first frozen, typically to $-40°$ to $-50°$ C.; the ice is then removed by sublimation under vacuum and at low sub-zero temperatures, following which the residual moisture which may amount up to 50% of the "dried" preparation is removed by desorption during which the temperature gradually rises. The complete freeze-drying cycle may take several days and is costly in capital and energy. Freeze-drying also suffers from technical disadvantages because of its irreproducibility. Suppliers of freeze-dried protein products generally specify storage at $-20°$ C. rather than ambient temperature. Exposure to ambient temperatures for periods of days to weeks can result in significant activity losses.

(v) Undercooling, as described in European Patent 0 136 030 and by Hatley et al. (Process Biochem. 22 169 (1987)) allows for the long-term (years) stabilisation of proteins without the need for additives. However, while this process extended the previous repertoire of possibilities, the undercooled preparations need to be shipped at temperatures not exceeding $+5°$ C. and must be stored, preferably at $-20°$ C. They also have to be recovered from a water-in-oil dispersion prior to their final use.

It will thus be apparent that a stabilisation/storage process which enabled storage at ambient temperature would be very desirable, since it would avoid the need for low temperature storage entailed by existing processes. Hitherto, however, storage at ambient temperature has been impossible for many materials.

There would also be advantage in adding to the existing "repertoire" of processes for stabilisation and storage, because some of the existing processes are limited in their applications or entail accepting disadvantages such as a need to mix with a stabilising agent which is difficult to remove later.

There would furthermore be advantage in providing a more cost effective process than the current freeze-drying process.

We have found, surprisingly, that materials which are not stable when isolated and held in solution at room temperature can nevertheless be successfully incorporated into a glass formed from a water-soluble or water-swellable substance, and can later be recovered. While in the glass the material is immobilised and stable.

In a first aspect this invention provides a storable composition comprising at least one material to be stored, preferably selected from the group consisting of proteins, peptides, nucleosides, nucleotides and enzyme cofactors, dissolved in a water-soluble or water-swellable substance which is in an amorphous, glassy or (much less preferably) rubbery state.

As will be explained in more detail below, it is preferred that the composition displays a glass transition temperature of at least 20° C. preferably at least 30° C.

It may be desirable that the composition has a water content of not more than 4% by weight.

The invention may be utilised for stable storage of a single material, or for a mixture of materials which have little or no effect on each other.

However, in a development of this invention, a single composition contains a plurality of materials which form part or all of a reacting system. These may be fairly simple chemicals.

In a further aspect, this invention provides a method of rendering a material suitable for storage, comprising dissolving the material in a water-soluble or water-swellable substance or solution thereof and forming the resulting mixture into a glass.

This process is capable of being carried out without the use of any non-aqueous organic solvent, which is advantageous because such solvent could prove harmful to many substances. Also processing with and/or removal of organic solvents can be undesirable for environmental reasons.

A further feature is that the process is energy efficient, requiring much less energy than freeze drying. Most of the drying can be done at less than 40° C.

MATERIAL STORED

The material(s) stabilized for storage may potentially be any of a wide range of materials which are ordinarily liable to undergo a chemical reaction which is dependent on diffusion of reacting species.

One category of materials to which the invention is applicable is proteins and peptides, including derivatives thereof such as glycoproteins. Such proteins and peptides may be any of: enzymes, transport proteins, e.g. haemoglobin, immunoglobulins, hormones, blood clotting factors and pharmacologically active proteins or peptides.

Another category of materials to which the invention is applicable comprises nucleosides, nucleotides, dinucleotides, oligonucleotides (say containing up to four nucleotides) and also enzyme cofactors, whether or not these are nucleotides. Enzyme substrates in general are materials to which the invention may be applied.

The material for stabilisation and storage may be isolated from a natural source, animal, plant, fungal or bacterial, or may be produced by and isolated from cells grown by fermentation in artificial culture. Such cells may or may not be genetically transformed cells.

The material will need to be soluble in aqueous solution, at least to the extent of forming a dilute solution which can be used for incorporation into the glass forming substance.

As mentioned above, a development of this invention is to store more than one component of a reacting system in a glass. This can be useful for materials which will be required to be used together in, for example, an assay or a diagnostic kit.

Storing the materials as a single glassy preparation provides them in a convenient form for eventual use. For instance, if an assay requires a combination of a substrate, or cofactor and an enzyme, two or all three could be stored in a glass in the required concentration ratio and be ready for use in the assay.

If multiple materials are stored, they may be mixed together in an aqueous solution and then incorporated together into a glass. Alternatively they may be incorporated individually into separate glasses which are then mixed together.

When multiple materials are stored as a single composition (which may be two glasses mixed together) one or more of the materials may be a protein, peptide, nucleoside, nucleotide or enzyme cofactor. It is also possible that the materials may be simpler species. For instance a standard assay procedure may require pyruvate and NADH to be present together. Both can be stored alone with acceptable stability. However, when brought together in aqueous solution they begin to react. If put together in required proportions in the glassy state they do not react and the glass can be stored.

THE GLASS-FORMING SUBSTANCE

A glass is defined as an undercooled liquid with a very high viscosity, that is to say at least $10^{13}$ Pa.s, probably $10^{14}$ Pa.s or more.

Normally a glass presents the appearance of a homogeneous, transparent, brittle solid which can be ground or milled to a powder. In a glass, diffusive processes take place at extremely low rates, such as microns per year. Chemical or biochemical changes including more than one reacting moiety are practically inhibited.

Above a temperature known a the glass transition temperature $T_g$, the viscosity drops rapidly and the glass turns into a rubber, then into a deformable plastic which at even higher temperatures turns into a fluid.

The glass forming substance employed in this invention must be hydrophilic—either water-soluble or water-swellable—so that water will act as a plasticiser. Many hydrophilic materials, both of a monomeric and a polymeric nature either exist as or can be converted into amorphous states which exhibit the glass/rubber transitions characteristic of amorphous macromolecules. They have well defined glass transition temperatures $T_g$ which depend on the molecular weight and a molecular complexity of the glass forming substance. $T_g$ is depressed by the addition of diluents. Water is the universal plasticiser for all such hydrophilic materials. Therefore, the glass/rubber transition temperature is adjustable by the addition of water or an aqueous solution.

For this invention it will generally be necessary that the glass forming substance, when anhydrous or nearly so, displays a glass transition temperature $T_g$ in a range from 20 to 150° C., preferably 25 to 70° C. If $T_g$ is towards the higher end of the range, a lower $T_g$ can be achieved by adding water which can be removed after the material which is to be stored has been incorporated into the glass. Mixtures of glass forming substances may be used if the components are miscible as a solid solution. If so, material(s) of lower $T_g$ serve as plasticiser(s) for material(s) of higher $T_g$.

If $T_g$ of the final composition is sufficiently high, storage can be at room temperature. However, if $T_g$ of the composition is close to or below room temperature it may be necessary or desirable to refrigerate the glassy composition if storage is for a prolonged period. This is less convenient but still is more economical than freeze-drying.

If the composition is heated above its $T_g$ during storage, it will change to its rubbery state. Even in this condition stored materials are stable for a considerable period of time. Consequently, it may well do no harm if the temperature of the stored material is allowed to go above $T_g$ for a limited time, such as during transportation.

If a composition is maintained above its $T_g$ (and therefore in a rubbery condition) the storage life will be limited but still considerable and the benefit of the invention will be obtained to a reduced extent.

Conversely, if $T_g$ of the composition is well above room temperature, the composition is better able to withstand storage at an elevated temperature, e.g. in a hot climate.

As mentioned above, $T_g$ of the formulated composition is typically 5° below $T_g$ of the anhydrous glass forming substance.

The glass forming substance should be sufficiently chemically inert towards the material which is to be incorporated in it. An absolute absence of chemical reactivity may not be essential, as long as it is possible to incorporate the material, store the glass, and recover the material without serious degradation through chemical reaction.

Many organic substances and mixtures of substances will form a glassy state on cooling from a melt.

Carbohydrates are an important group of glass forming substances: thus candy is a glassy form of sugar (glucose or sucrose). The $T_g$ for glucose, maltose and maltotriose are respectively 31, 43 and 76° C. (L. Slade and H. Levine, Non-equilibrium behaviour of small carbohydrate-water systems, Pure Appl. Chem. 60 1841 (1988)). Water depresses $T_g$ and for these carbohydrates the depression of $T_g$ by small amounts of moisture is approximately 6° C. for each percent of moisture added. We have determined the $T_g$ value for sucrose as 55° C.

In addition to straightforward carbohydrates, other polyhydroxy compounds can be used, such as carbohydrate derivates like sorbitol and chemically modified carbohydrates.

Another important class of glass forming substances are water-soluble or water-swellable synthetic polymers, such as polyvinyl pyrrolidone, polyacrylamide or polyethyleneimine. Here $T_g$ is a function of the molecular weight. Both of these classes of glass forming substances are suitable for the present invention.

A group of glass forming substances which may in particular be employed are sugar copolymers described in U.S. Pat. No. 3,300,474 and sold by Pharmacia under the Registered Trade Mark "Ficoll". This U.S. patent describes the materials as having molecular weight 5,000 to 1,000,000 and containing sucrose residues linked through ether bridges to bifunctional groups. Such groups may be alkylene of 2, 3 or more carbon atoms but not normally more than 10 carbon atoms. The bifunctional groups serve to connect sugar residues together. These polymers may for example be made by reaction of the sugar with a halohydrin or a bis-epoxy compound.

One process of rendering a material storage stable in accordance with the present invention commences from an aqueous solution of the material (which will be referred to as the active material), and a supply of the substance into which it is to be incorporated, with this substance already in an amorphous state, either glassy or rubbery.

Then a controlled amount of an aqueous solution containing the active material is incorporated into the glassy substance, thus turning it into a rubber: the materials are mixed to homogenise the glass forming substance with the active material. The rubbery form has the consistency of a dough and can be rolled or milled into a thin sheet. This rubber is then subjected to reduced pressure, possibly accompanied by moderate heat, in order to remove most of the added moisture. The final product is a glass with a glass temperature slightly, e.g. approximately 5°, below that of the pure glass forming substance. It can be kept in the form of a transparent film or ground into a fine powder or compressed into tablet form. In the glassy state (below $T_g$) the deterioration of the active material, by whatever mechanism, is retarded to the extent that, on practical time-scales, even substances which in their free states are extremely labile are found to possess long shelf-lives.

Full biochemical activity is maintained, but locked in, throughout this period at temperatures below $T_g$ and can be rapidly released by resolubilization of the glass in an aqueous medium.

The glass forming substance and the amount of solution added to it are chosen so that the rubbery material obtained from the addition is at a temperature above its $T_g$ (or to put it another way, its $T_g$ is below the ambient temperature) but as moisture is removed the value of $T_g$ increases to above the ambient temperature.

Preferably the starting substance also has its $T_g$ above ambient temperature, so that lowering of $T_g$ on addition of aqueous solution lowers this value from above ambient to below. However, it would be conceivable to begin with a moisture-containing substance whose $T_g$ already lies below ambient, lower it further through addition of aqueous solution of the material to be incorporated, and finally raise $T_g$ to above ambient temperature on drying.

The amount of aqueous solution which can and should be added to form a rubbery dough may well be found by trial and error. It is likely to be not more than 5% by weight based on the glass forming substance. The steps of adding solution to form a rubbery dough and drying this back to a glassy state can be repeated to build up the concentration of active material in the glass.

If desired, the $T_g$ value of a sample of a glass forming substance can be determined, and determined again after mixing in varying amounts of water, so as to be able to plot a graph of $T_g$ against moisture content.

$T_g$ values can be determined with a differential scanning calorimeter and can be detected as a point at which a plot of heat input against temperature passes through an inflection point—giving a maximum of the first temperature derivative.

Vacuum applied to assist the removal of water from the rubbery composition need not be particularly hard. Suitably it is less than 90% of normal atmospheric pressure. A pressure which is 80% of normal atmospheric pressure has been found adequate. A harder vacuum may be employed, however, if this is found convenient.

Heating of the doughy mixture to remove moisture may be at a temperature not above 80°, and for a protein is preferably not above 60° C. Heating may not be necessary: evaporation of moisture under reduced pressure may proceed to a sufficiently low moisture content even at room temperature of around 20° C., but of course heat accelerates the evaporation.

Another process for rendering material storage stable in accordance with the present invention can enable the material to be stored and recovered at a greater concentration of active material relative to the carrier substance. In this process a quantity of the carrier substance, or a solution thereof, is added to a solution of the active material. When the added carrier substance has dissolved fully, the solution may be divided into convenient portions, e.g. 0.1 to 1 ml. The samples of solution are placed under reduced pressure so that water is evaporated from them until the carrier substance is in a glassy state. Typical conditions are to commence the evaporation at a temperature not exceeding 40° C., preferably in the range from 20 to 30° C. and continue it for some hours, for instance 24 to 36 hours. As evaporation continues the glass temperature of the residual material rises. Evaporation for the period indicated can be sufficient to achieve a glass transition temperature exceeding 30° C. Once such a sufficiently high glass transition temperature has been achieved the temperature may be raised while evaporation continues. For instance once the glass transition temperature has reached a level of 30° C. the temperature may be raised to within a range of 40 to 70° C., e.g. 60° C. for a shorter time such as two hours. For this procedure also, vacuum used to bring about evaporation of water does not need to be particularly hard. It may also be found that heating is unnecessary: evaporation without heating for an extended time may achieve a sufficiently low moisture content.

In the above, the carrier substance may be added in a dry state, e.g. a powder, or as a solution.

Recovery (i.e. reactivation) of stored material can be effected by simply adding water or aqueous solution to a quantity of the glass with the active material therein. If the carrier substance is water-soluble the result is a solution of the material and the carrier substance.

Separation by chromatography to isolate the stored, active material from the glass forming substance is possible. However, in general it will be neither desirable nor necessary. Instead the glass forming substance is chosen so that it will not interfere with the use (e.g. assay) of the stored, active material.

In the case of a water-swellable glass forming substance, it will remain out of solution, perhaps as a gel, and the solution of the material can be separated by centrifugation if required.

The suitability of an intended glass forming substance and conditions for incorporation of material into it can both be checked by preparing a glass with the material incorporated, and then recovering the material without any substantial period of storage.

Storage stability can, if desired, be tested by storage at a higher temperature such as 35° C. or even 50° C. which gives an accelerated test.

EXAMPLES

In the examples which follow, Examples 1 to 4 illustrate the first process referred to above in which a solution containing the active material is incorporated into the glassy carrier substance, turning it temporarily into a rubbery state. Examples 5 onwards illustrate the second process described above in which the carrier substance is added to a solution of the active material and the resulting solution is then evaporated to the glassy state.

In some of the Examples, material is stored at a temperature above ambient, to provide an accelerated test of storage life.

Examples 1 and 2 describe the storage of lactate dehydrogenase (LDH) which is assayed using a combination of NADH and pyruvate. Example 4 shows the storage of the unstable mixture of NADH with pyruvate. This would provide a suitable material for use in carrying out LDH assays, but in Example 4 that assay procedure is used to confirm the activity of the NADH/pyruvate after storage.

Example 3 describes storage of restriction enzyme, and the activity of the stored enzyme is confirmed by showing that its effect on DNA remains unchanged.

EXAMPLE 1

The glass forming substance employed was Ficoll 400 DL (Pharmacia, Reg. Trade Mark) which is a copolymer of sucrose and epichlorohydrin. It is water-soluble and has a $T_g$ of 97° C. 4 grams of the Ficoll was weighed ($w_s$) into a dry Universal tube. About 50% was placed into a dry mortar and 0.2 ml of a solution containing 1,000 units/ml lactate dehydrogenase LDH (ex rabbit muscle) in 0.01M phosphate buffer pH 7.0 was added and mixed well into the Ficoll. A further 0.2 ml of LDH solution was then incorporated into the mix. A small amount of Ficoll was added, until a dough was obtained which did not adhere to the pestle. The dough was rolled out on a tile to give a sheet of approx 1 mm thickness. It was separated from the tile with a knife and lightly replaced onto the tile which was then heated in an oven for 30 minutes at 45–50° C. The sheet was removed from the oven and ground to a fine free-flowing powder which was stored in a sealed tube. The unused Ficoll was weighed ($w_e$). The powder containing the LDH was stored in the laboratory where temperatures fluctuated between 20 and 35° C.

The LDH activity of the powder, assuming no loss of LDH activity, should be given by the relationship:

$$LDH \text{ activity (units/grams)} = \text{approx} \frac{0.4 \, I}{(w_s - w_e)}$$

where I is the initial concentration of LD in the solution in units/ml.

The actual LDH activity of the powder was assayed. On the assumption that the powder contained negligible moisture, the powder was dissolved in phosphate buffer (0.01M pH 7) to give a test solution calculated to be a 1 to 1,000 dilution of the original solution. This would contain 1 unit of LDH per ml if enzyme activity was entirely preserved. Its actual activity was determined by the following procedure (Hatley, Franks and Mathias, Process Biochemistry, December 1987 page 170).

2.7ml of 0.01M phosphate buffer pH 7, 0.1 ml of 2 mg ml$^{-1}$ NADH, and 0.1 ml of 10 mM pyruvate were placed into a cuvette of path length 10 mm. The cuvette was capped and shaken. 0.1 ml of the test solution was added and the cuvette again capped and shaken. The absorbance at 340 nm was recorded at 30 second intervals for a total period of three minutes. The temperature of the solution was also noted. A period during which the absorbance change was linear with time was selected and the absorbance change per minute, $\Delta A$, calculated. The enzyme activity was calculated as follows:

$$LDH \text{ activity (units per milligram)} = \frac{\Delta A \cdot TCF}{6.25 \times C}$$

where:

$\Delta A$ = the absorbance change per minute at 340 nm.

6.25 = a correction factor for the molar absorbance of NADH.

TCF = a temperature correction factor which must be applied for assays performed at temperatures other than 25° C.

C = the concentration of the protein (mg ml$^{-1}$). No loss of LDH activity could be detected after storage for 5 months.

The stability of the product was compared to that of a commercial LDH preparation in 2.1M ammonium sulphate (Type II, 10,000 units/ml ex Sigma) which was stored at 25° C. and assayed periodically by the above method. The activity of this commercial preparation decreased on average by 1.2% per day over the first 45 days.

EXAMPLE 2

A quantity of crystalline sucrose was gently heated to melting on a hotplate under a dry, oxygen-free atmosphere. (Dry nitrogen was used). The sucrose was allowed to cool to give a transparent glass and was then ground into a fine powder, still under a dry atmosphere, and stored in a stoppered tube. 0.4 ml of an LDH solution, containing 4,000 units/ml, in 0.01M phosphate buffer pH 7.0 was added to 4 g of the sucrose glass and mixed using a pestle and mortar. The resulting paste was rolled out on a tile into a thin sheet which was then freed from, and lightly replaced on the tile. It was next heated in an oven for 30 minutes at 40–50° C. after which it was allowed to cool. It was then ground into a fine, free-flowing powder, all operations being performed under the exclusion of moisture. The powder was stored in an air-tight stoppered tube at 25° C. The LDH activity of the powder, assuming no loss of activity, should be given by:

LDH activity (units/g solid product) = approx 0.1 I where I is the initial LDH activity (units/ml) in the solution used to prepare the glass.

The preparation was assayed periodically for LDH activity, as described in Example 1. No loss of activity could be detected after 1 month storage at 25° C.

The glass temperature of the preparation was determined by differential scanning calorimetry as 32° C.

EXAMPLE 3

To 1 g Ficoll 400 were added 100 μl of a solution of EcoR I restriction endonuclease in 50% aqueous glycerol and a glass was prepared as described in Example 1. The final preparation was stored for 10 days in the laboratory with temperatures fluctuating between 20 and 30° C.

A quantity of the preparation equivalent to 2 units of enzyme, based on the assumption that the enzyme was still fully active, was dissolved in the following buffer: 100 mM Tris-HCl pH 7.5, 10 mM $MgCl_2$, 50 mM NaCl, 0.1 mg/ml bovine serum albumin. An assay for enzyme activity was carried out by the following procedure (which is taken from LKB Laboratory Manual: LKB 2013 Miniphor Submarine Electrophoresis Unit 1985, Chapter 6). The solution was incubated with 1 μg lamda-DNA for 1 hour at 37° C. Electrophoresis of the incubation mixture was then carried out on 0.5% agarose gel in Tris/borate buffer in standard manner. The DNA breakdown bands observed on the gel corresponded exactly with those of a control run with a fresh enzyme solution.

EXAMPLE 4

A solution containing 100 mg/ml NADH and 33 mg/ml pyruvate was prepared. 0.4 ml of this solution were incorporated into 4 g of a sucrose glass and the mixture processed, as described in Example 2. The mixed glass was stored in 20 mg quantities in spectrophotometer cuvettes which were closed with sealing film and kept in a laboratory where the temperature fluctuated between 20 and 35° C. The glass was stored for 14 days.

For purposes of assay, the contents of a cuvette were dissolved in 2.7ml of 0.01M phosphate buffer (pH 7.0) and 0.1 ml of a LDH solution containing 1 unit/ml was added. The absorbance at 340 nm was recorded at 30 second intervals for a total period of 3 minutes and the temperature of the solution was measured. The apparent LDH enzyme activity was determined from the period during which the absorbance change was linear with time. The activity was calculated as in Example 1. A control assay was carried out with fresh solutions of NADH and pyruvate. The apparent activity obtained using the dissolved glass closely matched the control value.

EXAMPLE 5

The active material was glutamate dehydrogenase. 532 mg of Ficoll 400 DL as used in Example 1 was added to 20 ml of a glutamate dehydrogenase solution, containing 13.3 mg/ml protein. The protein:Ficoll ratio was therefore 1:2. The sample was then divided into eighty 0.25 ml portions and dried at 37° C. under reduced pressure (about 80% of atmospheric) for 24 hours. The sample was then divided into two batches of 40 vials. One batch was heated under reduced pressure for a further two hours at 60° C. The batches were then further subdivided and stored under a range of conditions (see below). Vials were periodically rehydrated by adding 2.23 ml of 50 mM Tris/HCl buffer at pH 7.5, containing 0.3 mM EDTA to give a solution which, assuming no loss of activity, would have contained 100 units of enzyme per ml. This was serially diluted to 1 unit/ml in the same buffer. The actual activity of the recovered enzyme was determined. The assay procedure for recovered enzyme made use of the following solutions:

Solutions
1. 50 mM Tris/HCL pH 7.5+0.3 mM EDTA
2. 4.5 mg/ml NADH in solution 1
3. 4.0125 g $NH_4Cl$ in 25 ml $H_2O$
4. 97 mg α-ketoglutarate (disodium salt) in 50 ml solution 1.

To carry out the assay 2.6 ml of solution 4, 0.2 ml of solution 3 and 0.1 ml of solution 2 were mixed in a 3 ml cuvette. 0.1 ml of the recovered enzymes solution was added. The absorbance at 340 nm was observed over 5 minutes and the activity of the enzyme calculated from the change (ΔA) in absorbance during the 5 minute period. Activity was calculated using the following formula:

$$\text{Activity (units/ml)} = \frac{\Delta A \times 3}{5 \times 0.622}$$

The results obtained are set out in the following Table in which "initial activity" denotes the activity of enzyme which was recovered after only a minimal period of storage. The activities are quoted as percentages of the theoretical value of activity assuming this had been retained fully. A quantity of a commercially freeze-dried glutamate dehydrogenase (whose activity before freeze drying was stated by the supplier) was divided into several portions and stored at 25° C. for varying periods and assayed in the same way. Its activity is also quoted as percentages of the theoretical activity. The results for this material ar included in the Table.

| Process Temperature | Storage Temperature | Initial Activity | Duration of Storage (weeks) | | | | | |
|---|---|---|---|---|---|---|---|---|
| | | | 1 | 2 | 3 | 4 | 6 | 12 |
| 37° C. | ambient | 97% | 95% | 99% | | 98% | 86% | |
| 37° C. | 35° C. | 97% | 78% | 82% | | 87% | 84% | |
| 37° C. | 25° C. | 130% | 122% | 121% | 83% | 69% | | 74% |
| 60° C. | ambient | 103% | 109% | 96% | | 85% | 98% | 97% |
| 60° C. | 35° C. | 103% | 102% | 105% | | 96% | 116% | |
| 60° C. | 25° C. | 121% | 114% | 125% | 84% | 81% | | 89% |
| Freeze-dried | 25° C. | 56% | 40% | 35% | 33% | 36% | | |

As can be seen from these results, experimental error gives rise to some variation in FIGURES, but these do nevertheless show very substantial retention of activity over prolonged storage and much better retention of activity than with freeze-dried material.

EXAMPLE 6

2.50 ml of ascorbate oxidase (21.25 mg protein) solution was prepared. To this was added 2.50 ml of Tris buffer pH 7.6 containing 21.25 mg Ficoll 400, giving a protein:Ficoll weight ratio of 1:1. This was then divided into ten 0.5 ml portions and dried at 37° C. under reduced pressure of about 80% of atmospheric for 24 hours. The samples were next heated, still under reduced pressure, for a further two hours at 60° C. Storage was on a laboratory shelf (temperature fluctuations between 17 and 28° C.). After varying periods of storage, samples were rehydrated by addition of 2.5 ml of 0.4 mM $Na_2HPO_4$ containing 0.5% Bovine serum albumin. It was then serially diluted in more of the same solution so that its activity would be 0.2 units/ml, if activity had been fully retained, and assayed. The activity relative to the starting value was determined.

Assay was carried out using a standard assay procedure published by Boeringer Mannheim. The assay monitors the decrease in absorbance at 245 nm as the enzyme catalyses the oxidation of a known solution of ascorbic acid. Enzyme which had been stored for 2 months at 35° C. was found, within the limits of experimental error, to have the same activity as enzyme which was stored for only a very short time.

EXAMPLE 7

Lactate dehydrogenase was incorporated into Ficoll 400 using the procedure of Example 5. The Ficoll:enzyme ratio was 0.23:0.26. Samples were stored for various periods and then recovered by adding 0.01M phosphate buffer in a quantity which would give a theoretical activity of 1 unit/ml, assuming full retention of activity. The recovered solutions were assayed using the procedure set out in Example 1. The measured activity of recovered material, as a percentage of the theoretical activity was:

| Before Drying | Storage period (days) | | | | | |
|---|---|---|---|---|---|---|
| | 1 | 14 | 21 | 28 | 35 | 180 |
| 100% | 91% | 81% | 91% | 112% | 97% | 98% |

EXAMPLE 8

Cytochrome C reductase was incorporated into Ficoll 400 by the procedure of Example 5. The ratio of enzyme:Ficoll was 1:1. Samples were subjected to an accelerated test, viz. stored for 14 days at 35° C., and then recovered by adding 4 ml of 0.2M $KHCO_3$ to give a solution with a theoretical activity of 0.87 unit/ml assuming full retention of activity. The recovered material was assayed using a procedure given in "Methods in Enzymology" by Mahler, Volume II 1955 p. 688. It was found that the recovered material had an activity of 88% of the theoretical value.

EXAMPLE 9

Glycerol-3-phosphate dehydrogenase was incorporated into Ficoll 400 by the procedure of Examples. The ratio of enzyme:Ficoll was 1:2. Samples were subjected to an accelerated storage test by storage at 35° C. After 7 days storage the material was recovered by adding 0.05M Tris/HCl buffer at pH 7.6. This also contained 2 mg/ml albumin and 0.74 mg/ml EDTA. The recovered material was assayed using a procedure published by Biozyme Laboratories in which the enzyme catalyses the reaction:

dihydroxyacetone phosphate − NADH ⟶

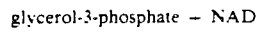
glycerol-3-phosphate − NAD and the oxidation of NADH is followed spectrophotometrically at 340 nm.

It was found that after 7 days storage at 35° C. the activity was 96% of the activity of a control sample which was rehydrated immediately after being incorporated into Ficoll.

EXAMPLE 10

Alpha-glucosidase was incorporated into Ficoll 400 using the procedure of Example 5. The Ficoll:enzyme ratio was 1:1. As an accelerated test, samples were stored for various periods at 35° C. and then recovered by adding 4 mls of 0.067M phosphate buffer at pH 7.0 to give a solution whose theoretical activity, assuming full retention of activity, was 2 units/ml. The recovered solutions were assayed by a procedure described by H. Halvorson, Methods in Enzymology 8 559 (1966). The actual activity of recovered material relative to the theoretical value was:

| Before Drying | Storage period (days at 35° C.) | | | |
|---|---|---|---|---|
| | 1 | 4 | 11 | 90 |
| 100% | 100% | 103% | 95% | 70% |

EXAMPLE 11

Pyruvate: 5 g of Ficoll 400 was added to 20 ml of 10 mM sodium pyruvate solution. The solution was then divided into 40 portions, each containing 0.25 ml portions and processed in the manner described for Example 5 to give glasses.

NADH: 5 g of Ficoll 400 was added to 20 ml of a 2 mg/ml NADH solution. This was divided into 40 portions, each containing 0.25 ml, and processed as in Example 5 to give glasses.

At intervals following storage one sample of each reagent was rehydrated and the solutions mixed. They were assayed by the standard method described in Example 4. After 3 months storage at ambient temperature their ability to react in the LDH assay was 100% of the control value obtained at the initiation of storage.

EXAMPLE 12

NADH and pyruvate were processed as in Example 11. Portions of each resulting glass powder were mixed together. One such mixture was at once rehydrated and assayed by the procedure of Example 4. The reaction mixture consisted of 2.8 mls 0.01M phosphate buffer, 0.1 ml of rehydrated NADH/pyruvate mixture, and 0.1 mls of 1 unit/ml enzyme solution. The change in absorbance at 340 nm over three minutes was defined as 100%.

A further mixture was stored for one week and then rehydrated and assayed in the same way. Within the limits of experimental error, its activity was the same. Thus there had been no reaction of the NADH and pyruvate during storage.

EXAMPLE 13

A range of carrier materials were used in a standard procedure in which the stored active material is lactate dehydrogenase. In each case, a solution consisting of 0.05 g of carrier dissolved in 100 ml 0.01M phosphate buffer was prepared. 1 ml of 10 mg/ml lactate dehydrogenase solution was then added to 20 ml of the prepared solution. The solution thus created was divided into 0.5 ml aliquots in glass vials. These were dried under reduced pressure of about 80% atmospheric in a vacuum oven at 36° C. for 24 hours. After drying the vials were sealed and stored at ambient temperature. The product had a carrier:protein ratio by weight of 1:0.22.

Some samples were rehydrated immediately by addition of phosphate buffer. Others were stored for various lengths of time and then rehydrated. The activity of enzyme was determined as in Example 1. Activity of enzyme is expressed, in each case, as activity relative to that of enzyme rehydrated in the first week after drying. Results are set out in the following Table, in which "PVP" denotes polyvinylpyrollidone, "GPS" denotes 6-O-α-D-glucopyranosyl-D-sorbitol. "Palatinit" is a product of Südzucker Aktiengesellschaft, Mannheim-Ochsenfurt, Germany, and consisting of an equimolecular mixture of α-D-glucopyranosyl-1,6-mannitol and α-D-glucopyranosyl-1,6-sorbitol.

| Carrier | \multicolumn{10}{c}{Storage period at 25° C. (weeks)} |
|---|---|---|---|---|---|---|---|---|---|---|
|  | 1 | 2 | 3 | 4 | 5 | 6 | 8 | 10 | 12 | 16 |
| Maltotriose | 100 | 114 |  | 91 |  | 96 | 68 | 71 | 101 | 94 |
| Polydextrose | 100 | 132 |  | 123 |  | 103 | 116 | 146 | 103 |  |
| Inulin | 100 | 99 |  | 91 |  | 95 | 114 | 98 | 91 |  |
| Stachyose | 100 | 122 |  | 137 |  | 140 | 109 | 106 | 127 |  |
| Dextran | 100 | 81 |  | 71 |  | 89 | 102 | 91 | 95 | 84 |
| Sorbose | 100 | 93 | 75 | 76 |  | 55 | 66 | 65 | 58 | 62 |
| Polyacrylamide | 100 | 100 | 80 |  | 71 |  | 53 | 62 | 55 | 63 |
| PVP | 100 | 75 |  | 76 |  | 70 | 62 |  |  |  |
| GPS | 100 | 124 |  |  |  |  |  |  |  |  |
| Palatinit | 100 | 99 |  |  |  |  |  |  |  |  |

We claim:

1. A composition which is storage stable at 20° C. comprising:
   i) a carrier substance which is water-soluble or water-swellable and is in a glassy amorpous state;
   ii) at least one material to be stored, which is unstable in aqueous solution at room temperature of 20° C. dissolved in said amorphous carrier substance, said composition existing in a glassy state at 20° C.

2. A composition according to claim 1 wherein the material to be stored is selected from proteins, peptides, nucleosides, nucleotides, dimers or oligomers of nucleosides or nucleotides, enzyme cofactors, and derivatives of any of the foregoing having one or more additional moieties bound thereto.

3. A composition according to claim 1 having a water content not exceeding 4% by weight.

4. A composition according to claim 1 wherein the composition displays a glass transition temperature of at least 30° C.

5. A composition according to claim 1 wherein carrier substance is selected from carbohydrates and derivatives thereof which are polyhydroxy compounds.

6. A composition according to claim 5 wherein the carrier substance is a sugar polymer containing sugar residues linked through ether bridges to bifunctional groups other than carbohydrate.

7. A composition according to claim 1 wherein the carrier substance is a synthetic polymer.

8. A composition according to claim 1 wherein said material to be stored comprises a material which is unstable when alone in aqueous solution at room temperature.

9. A composition according to claim 1 wherein said material to be stored comprises a plurality of materials.

10. A composition according to claim 9 wherein said material to be stored comprises a plurality of materials which react together in aqueous solution.

11. A composition according to claim 1 which can be stored without refrigeration for at least 1 week.

12. A method of rendering a material storage stable at 20° C., which material is unstable in aqueous solution at room temperature of 20° C., comprising dissolving the material in a carrier substance which is water-soluble or water-swellable, or in a solution thereof, so that the material is dissolved in said carrier substance, and forming the resulting mixture into a glassy amorphous state, said mixture existing in said glassy state at 20° C.

13. A method according to claim 12 wherein forming the said mixture into an amorphous state is effected by evaporation under subatmospheric pressure.

14. A method according to claim 13 wherein evaporation is commenced at a temperature of 20 to 40° C. and subsequently continued at a temperature of 40 to 70° C.

15. A method according to claim 13 wherein the subatmospheric pressure is not greater than 90% of atmospheric.

16. In a method of storing a material, which material is unstable in aqueous solution at 20° C., the improvement comprising dissolving the material in a carrier substance which is water-soluble or water-swellable, or in a solution thereof, so that the material is dissolved in said carrier substance, forming the resulting mixture into a glassy amorphous state and storing the mixture in said glassy amorphous state without refrigeration for at least one week.

* * * * *